United States Patent [19]
Dadoo et al.

[11] Patent Number: 5,342,492
[45] Date of Patent: Aug. 30, 1994

[54] SYSTEM FOR ELECTROKINETIC SEPARATION AND DETECTION WHERE DETECTION IS PERFORMED AT OTHER THAN SEPARATION ELECTRIC FIELD

[75] Inventors: Rajeev Dadoo; Richard N. Zare, both of Stanford, Calif.; Luis A. Colon, Williamsvile, N.Y.

[73] Assignee: The Board of Trustees of the Leland Stanford Junior University, Stanford, Calif.

[21] Appl. No.: 115,466

[22] Filed: Sep. 1, 1993

[51] Int. Cl.[5] .................... G01N 27/26; G01N 27/447
[52] U.S. Cl. ................................ 204/180.1; 204/299 R
[58] Field of Search .......................... 204/299 R, 180.1

[56] References Cited

U.S. PATENT DOCUMENTS

| | | | |
|---|---|---|---|
| 4,909,919 | 3/1990 | Morris et al. | 204/299 R |
| 5,015,350 | 5/1991 | Wiktorowicz | 204/180.1 |
| 5,122,248 | 6/1992 | Karger et al. | 204/182.8 |
| 5,126,023 | 6/1992 | Huang et al. | 204/180.1 |
| 5,169,510 | 12/1992 | Lunte et al. | 204/299 R |

OTHER PUBLICATIONS

Susan Lunte et al "Detection of Carbohydrates by Capillary Electrophoresis with Pulsed Amperometric Detection" Analytical Chemistry, vol. 65, No. 7 (Apr. 1, 1993) 948–951.

Wenzhe Lu and Richard M. Cassidy "Evaluation of Ultramicroelectrodes for the Detection of Metal Ions Separated by Capillary Electrophoresis" analytical Chemistry, vol. 65, No. 13 (Jul. 1, 1993) 1649–1653.

"Capillary Zone Electrophoresis with Electrochemical Detection," by Wallingford et al., *Anal. Chem.*, 1987, 59, 1762–1766, no month available.

"End–Column Detection for Capillary Zone Electrophoresis," by Huang et al., *Anal. Chem.*, Jan. 1991, 63, 189–192.

"Enhanced Separation of DNA Restriction Fragments by Capillary Gel Electophoresis Using Field Strength Gradients," by Guttman et al., *Anal. Chem.*, Oct. 1992, 64, 2348–2351, Beckman Instruments Inc., Fullerton, Calif., 1992.

*Primary Examiner*—John Niebling
*Assistant Examiner*—John S. Starsiak, Jr.
*Attorney, Agent, or Firm*—Majestic, Parsons, Siebert & Hsue

[57] ABSTRACT

A voltage alternating between a high value and a low value is applied across a separation capillary in an electrophoretic system and electrochemical detection is performed only during time periods when a low voltage or no voltage is applied to the tube to improve the sensitivity of detection.

22 Claims, 3 Drawing Sheets

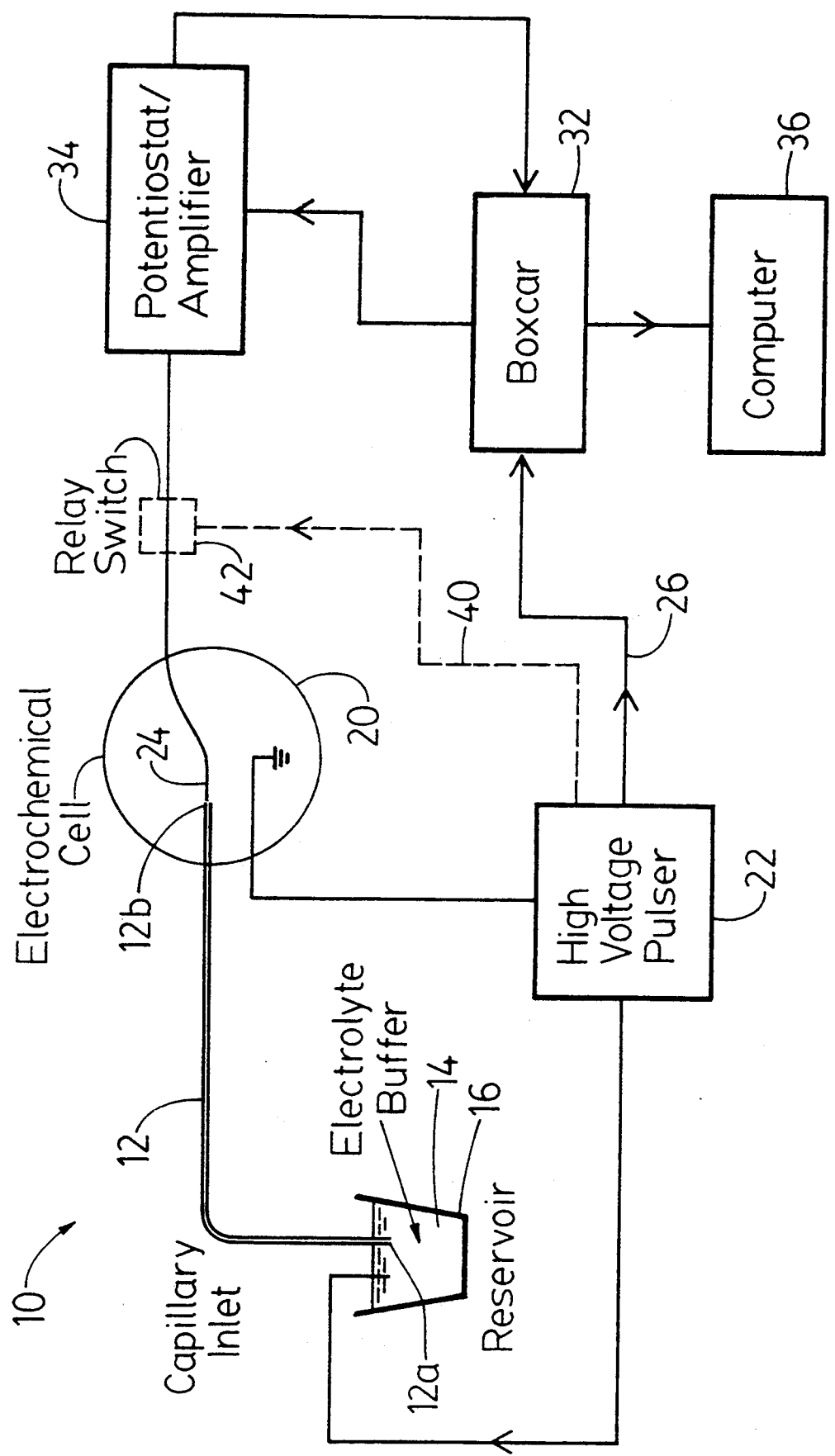
FIG._1.

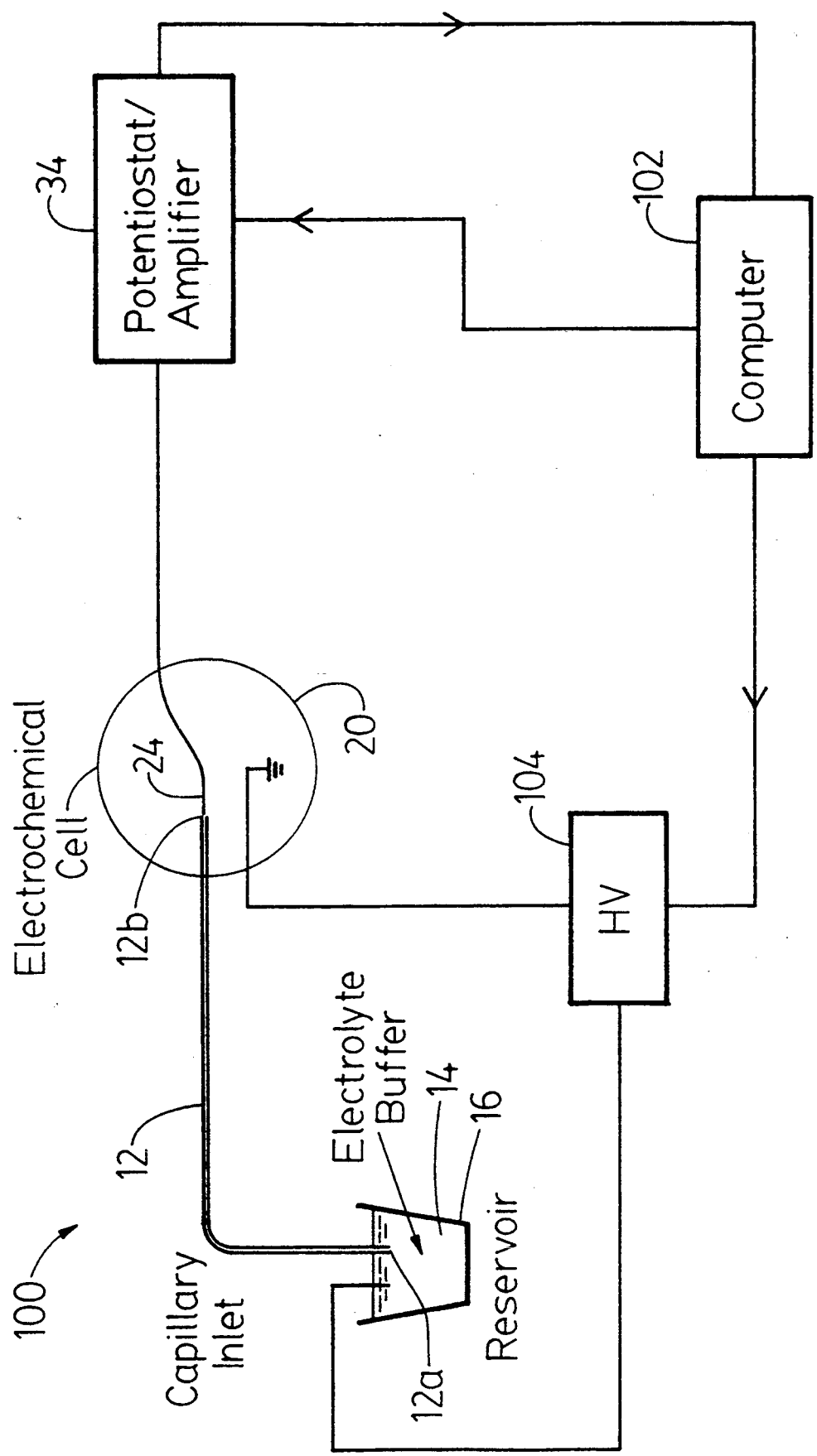
FIG._2.

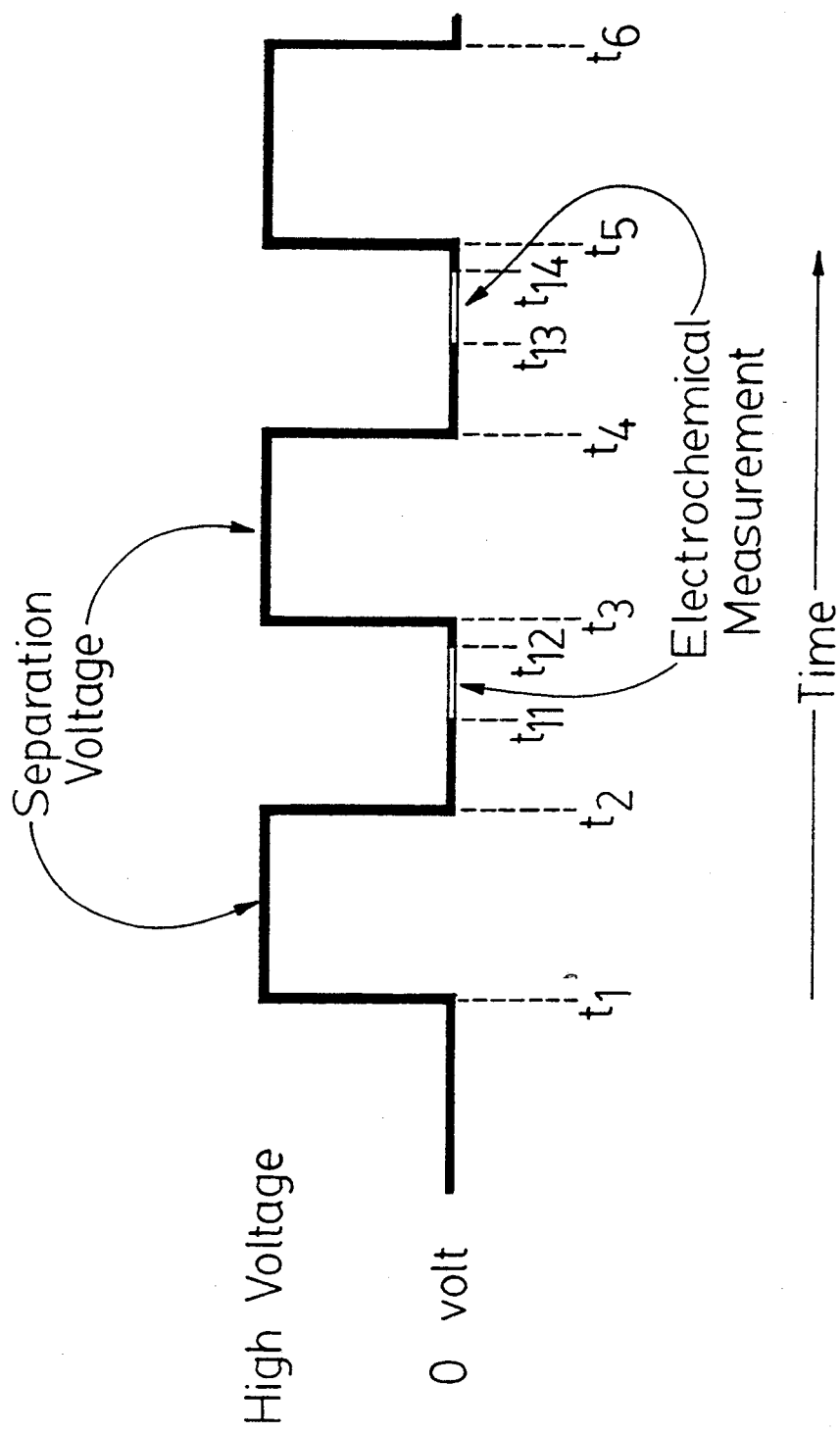
FIG._3.

SYSTEM FOR ELECTROKINETIC SEPARATION AND DETECTION WHERE DETECTION IS PERFORMED AT OTHER THAN SEPARATION ELECTRIC FIELD

BACKGROUND OF THE INVENTION

This invention relates in general to separation and detection techniques and, in particular, to a system for electrokinetic separation and detection.

Capillary separation techniques such as capillary electrophoresis (CE) involving gel or liquid columns have become important analytical techniques for the analysis of various complex sample mixtures. The sample mixtures analyzed are typically in tiny volumes, such as a few nanoliters or picoliters. When the samples are available in such tiny volumes, it is necessary to employ detection methods with high sensitivity. A number of detection methods have been in use. These include absorbance, fluorescence, chemiluminescence, radioactivity, mass spectrometric and electrochemical detection. Electrochemical detection can be amperometric or conductivity-based. Electrochemical detection has certain advantages over the other detection schemes that have been developed for CE. These include sensitivity (down to the attomole level) and selectivity for amperometric, and universality for conductivity, as known to those skilled in the art. An additional advantage in electrochemical detection is that a variety of compounds of interest (e.g., carbohydrates, amino acids, alcohols, etc.) can be detected without prior derivatization. It also utilizes relatively inexpensive instrumentation.

In CE, the separation electric field applied can range from 100 volts per cm to 1,000 volts per cm. With such a high magnitude electric field inside the separation column, one of the main problems in electrochemical detection is the isolation of the detection apparatus such as measuring electrodes and the associated electronics from the separation electric field. If the detection apparatus is not properly isolated from the separation electric field, the amperometric and conductivity measurements will be less sensitive to sample components at low concentration. A number of solutions have been proposed for this problem. In "Capillary Zone Electrophoresis with Electrochemical Detection," by Wallingford and Ewing, *Anal. Chem.*, 1987, 59, 1762–1766, a post-column electrochemical detection scheme is proposed for CE by grounding the separation capillary before detection. For this purpose, a porous glass coupler was built to connect two pieces of capillary together, where sample separation occurs in one piece of the capillary and detection occurs in the other piece of the capillary. This procedure is manually intensive and also degrades separation efficiency. End-column detection has also been proposed to minimize the effects of the separation voltage on CE-electrochemical detection. See Huang et al., *Anal. Chem.*, 1991, 63, 189 and U.S. Pat. No. 5,126,023. In end-column detection, the detection or measuring electrode is placed outside or at the end of the separation column. When the detection or measuring electrodes are placed at or near the end of the separation column, the background noise can be substantial due to the high current in the separation column where such background noise may overwhelm measurements to be taken. For this reason, high resistivity buffers are frequently used in conjunction with the end-column detection scheme to reduce both the amount of current at the end of the column and the background noise. The requirement of high resistivity buffers, however, limits the type of buffers that can be used and therefore the separation capabilities of CE as applied to certain samples. In both the post-column and end-column detection schemes, detection noise has been observed to increase with an increase in separation voltage.

From the above, none of the solutions proposed for the problem of isolating the detection apparatus from the separation electric fields is entirely satisfactory. It is therefore desirable to provide an improved capillary electrophoretic system where the above-described difficulties are alleviated or eliminated.

SUMMARY OF THE INVENTION

This invention is based on the observation that the above-described difficulties in electrochemical detection as applied to CE can be reduced or eliminated if detection measurements are made only when the separation electric field has been lowered to below a predetermined value. At the time or times when detection is not performed, a high magnitude electric field is applied to accomplish electrophoretic separation.

One aspect of the invention is directed towards a method for electrokinetic separation and detection, comprising introducing a sample to be separated into a capillary tube and applying an electrical potential across a portion of the capillary tube to cause electrokinetic separation of the sample into its components. The applying step is such that magnitude of the electrical field in a section of the tube is intermittently below a predetermined value for a plurality of time periods, and is above said predetermined value at other time periods. The method further comprises intermittently measuring at least one electrochemical parameter of the separated components during said plurality of time periods.

Another aspect of the invention is directed towards a method for electrokinetic separation and detection comprising introducing a sample to be separated into a capillary tube and applying an electrical field in a portion of the capillary tube to cause electrochemical separation of the sample into its components such that during at least one time period when the electrical field is applied, the electrical field in a section of the tube has a magnitude that is less than about one-fifth of the magnitude of the electrical field at other times or time periods when the electrical field is applied. The method further comprises measuring at least one electrochemical parameter of the separated components during said at least one time period.

An additional aspect of the invention is directed towards an apparatus for electrokinetic separation and detection comprising a capillary tube and a first device introducing a sample to be separated into the capillary tube. The apparatus further includes a second device for applying in it an electrical field across a portion of the capillary tube to cause electrokinetic separation of the sample into its components. The second device is such that the magnitude of the electrical field in a section of the tube is intermittently below a predetermined value for a plurality of time periods, and is above said predetermined value at other time periods. The apparatus further includes a third device for intermittently measuring at least one electrochemical parameter of the separated components during said plurality of time periods.

Yet another aspect of the invention is directed towards an apparatus for electrokinetic separation and detection comprising means for introducing a sample to be separated into a capillary tube and a device for applying an electrical field in the section of the capillary tube to cause electrokinetic separation of the sample into its components such that during at least one time period when the electrical field is applied, the electrical field has a magnitude that is less than about one-fifth of the magnitude of the electrical field at other times or time periods when the electrical field is applied. The apparatus further includes a third device for measuring at least one electrochemical parameter of the separated components during said at least one time period.

BRIEF DESCRIPTION OF THE DRAWINGS

FIG. 1 is a schematic view of a capillary electrophoretic system employing a high voltage pulser and a boxcar to illustrate a first embodiment of the invention.

FIG. 2 is a schematic view of a capillary electrophoretic system employing electrochemical detection and a computer for controlling the high voltage to illustrate a second embodiment of the invention.

FIG. 3 is a graphical illustration of a voltage applied across the separation channel of a capillary electrophoretic system to illustrate the invention.

DETAILED DESCRIPTION OF THE PREFERRED EMBODIMENT

FIG. 1 is a schematic view of a capillary electrophoretic system employing a high voltage pulser, and a boxcar as well as other instruments to illustrate the first embodiment of the invention. As shown in FIG. 1, apparatus 10 includes a capillary tube 12 with an inlet end 12a and an outlet end 12b. An electrolyte buffer 14 is supplied to the tube to end 12a from a reservoir 16. The electrolyte buffer which exits from outlet end 12b passes through an electrochemical cell 20.

As is known in conventional capillary electrophoresis, a sample is introduced into the inlet end 12a, such as by dipping end 12a for a short time into a sample and applying a voltage across the tube to move a small portion of the sample into the tube. The end 12a is then dipped into the reservoir 16. A high voltage is applied between reservoir 16 and cell 20 by means of a high voltage supply 22, where the portion of the sample is then carried under the influence of the electric field through tube 12 towards end 12b. As is also known in the electrophoretic art, different components of the sample may move with different speeds in tube 12, causing the components to separate along the length of the tube. These components are detected by working electrode 24 when the components exit end 12b into cell 20. Signals from electrode 24 are detected by a potentiostat/amplifier 34 for analysis and recording. As is known to those skilled in the art, a reference electrode (not shown) is usually also employed in cell 20 for amperometric and conductivity measurements.

The construction of electrochemical cell 20 is known to those skilled in the art and will not be described in detail here. One example of such cell is shown in FIG. 2 of the above-referenced article by Wallingford et al.

As explained above, the electric field applied to tube 12 to cause the sample to separate is usually quite high, typically of the order of 100 volts to a few kilovolts per centimeter. Therefore, such high magnitude electric field may adversely affect the small amplitude signals detected by electrode 24. As discussed above, none of the above referenced post-column and end-column detection schemes is entirely satisfactory. This invention is based on the observation that, by applying an electrical field that has at least two different magnitudes at different times, one value being suitable for causing the sample to separate and the other value which is low enough to reduce noise in electrochemical measurements, the above-described disadvantages of prior art detection schemes can be avoided.

One embodiment of the invention will now be described in reference to FIGS. 1 and 3. FIG. 3 is a graphical illustration of the wave form of a voltage potential applied across ends 12a, 12b of tube 12 to cause sample separation. As shown in FIG. 3, during time periods t1–t2, t3–t4 and t5–t6, a high voltage is applied to cause the sample to separate. However, during the time periods in between, such as time periods t2–t3 and t4–t5, ground potential is applied to both cell 20 and reservoir 16. Electrochemical measurement is then performed only during such time periods when both reservoir 16 and cell 20 are at ground potential. This means that signals from electrode 24 are taken only when there is essentially zero or a very low electric field in tube 12 so that the measurements taken will be sensitive to sample components at low concentrations. As shown in FIG. 3, signals from electrode 24 are measured only during time periods t11–t12 and t13–t14 during the time periods when the electrolyte buffer at end 12a and at end 12b are at same ground potential.

The above-described voltage wave form and electrochemical measurement illustrated in FIG. 3 can be implemented by the apparatus 10 of FIG. 1. In reference to FIG. 1, high voltage pulser 22 applies a voltage potential of the type shown in FIG. 3 across reservoir 16 and cell 20. Pulser 22 also sends a signal along line 26 to boxcar 32 to indicate the rising edges of the high voltage at times t1, t3, t5 . . . , and to also indicate the falling edges of the high voltage at times t2, t4, t6, . . . . As known to those skilled in the art, boxcar 30 will then turn on or off the potentiostat/amplifier 34 that measures the signals detected by working electrode 24. For example, when the boxcar receives a signal from pulser 22 indicating the rising edges at times t1, t3, t5 . . . , the boxcar will then turn off the potentiostat/amplifier. Whereas when the boxcar receives a signal from pulser 22 indicating the falling edges at times t2, t4, t6 . . . , the boxcar will then turn on the potentiostat/amplifier. The signals detected by potentiostat/amplifier 34 from electrode 24 are then sent to boxcar 32 which in turn sends the signals to computer 36 for analysis or any other instrument suitable for analyzing the signals.

From the above, it is evident that even though electrode 24 is continuously detecting electrochemical parameters at or near end 12b of tube 12 in cell 20, the signals provided by electrode 24 are measured intermittently and only during time periods when there is no or a very low electric field in a section of tube 12 close to the electrode 24, where the time periods are between other time periods during which high electrical field is applied to the tube to separate the sample. The above result can also be achieved by a slightly modified scheme as indicated by the dotted line 40 in FIG. 1. Instead of sending a signal to boxcar 32 in order to turn on and off the potentiostat/amplifier, high voltage pulser 22 instead sends signals indicating the rising and falling edges as described above to a relay switch 42 so that signals indicating the rising edges of the high voltage would turn off the switch whereas signals indicating the falling edges of the high voltage would turn on the switch. In this manner, the potentiostat/amplifier 34 would received signals from electrode 24 only during the times when pulser 22 applies ground potential to both cell 20 and buffer 14 in reservoir 16.

As illustrated in FIG. 3, it may be desirable for measurements to be taken only towards the end of the time periods t2–t3 and t4–t5 when no electrical potential is applied across the tube, to allow a time delay period for the electrical field in the tube to decay where the time delay period is a function of the capacitance of the system. This is illustrated as time periods t11–t12 and t13–t14 in FIG. 3. When the boxcar 32 is used, a delay element may be incorporated in the boxcar to delay the turning on of potentiostat/amplifier 34 until a fixed time delay (such as delay t2–t11) after the boxcar receives a signal from pulser 22 indicating a falling edge of the high voltage in FIG. 3. If line 40 and relay switch 42 are used instead of the boxcar 32, such delay may be incorporated as part of the construction of switch 42 in a manner known to those skilled in the art. All such and other variations are within the scope of the invention.

FIG. 2 is a schematic view of a capillary electrophoretic system employing electrochemical detection and a computer for controlling the high voltage to illustrate a second embodiment of the invention. Instead of using a high voltage pulser and boxcar or relay switch as in FIG. 1, the above-described process for generating an intermittent high voltage and intermittent measurements of electrochemical parameters at low electrical fields may be performed by using computer control in the apparatus 100 as illustrated in FIG. 2. As shown in FIG. 2, computer 102 may be used to control a high voltage source 104 to cause the source 104 to apply a voltage potential across the two ends of tube 12 of the form shown in FIG. 3. Computer 102 then causes the potentiostat/amplifier 34 to be turned on only during time periods when high voltage 104 applies the same ground potential between the buffer 14 in reservoir 16 and that in cell 20. The signals detected by potentiostat/amplifier 34 are provided to the computer 102 directly for analysis. Instead of causing the potentiostat/amplifier 34 to be turned on and off as described above, computer 102 can instead leave the potentiostat/amplifier 34 on all the time by simply discarding the data signals from the potentiostat/amplifier obtained while a high voltage is applied across the capillary tube; this is also possible using the apparatus 10 of FIG. 1. For simplicity, identical components in the different figures of this application are labeled by the same numerals.

In order to minimize noise during electrochemical measurements, it would be desirable for the amplitude of any electric field in tube 12 to be as small as possible. It is understood, however, that such measurements can be made even though the electric field in tube 12 is not "0". For this reason, it is adequate that if during such measurements, the magnitude of the electric field in a section of tube 12 at or near electrode 24 (such as at end 12b) is below a predetermined value such as 100 volts per centimeter, even though at other time periods when no measurements of signals at electrode 24 are taken, the electric field exceeds such value.

Electric fields typically applied to separate a sample in electrophoresis are typically in the range of 100 volts to a few kilovolts per centimeter and the voltage across the two ends of the capillary typically ranges from a few kilovolts to 30 kilovolts for capillaries 20 to 100 centimeter in length. Therefore, it may also be adequate if, during at least one time period when electrical field is applied, the electrical field in the vicinity of the electrode 24 has a magnitude that is less than about one-fifth of the magnitude of the electrical field at other time(s) or time period(s) when the electrical field is applied.

As shown in FIG. 3, the voltage wave form applied alternates between a high voltage and zero volts at a certain frequency or duty cycle. While in FIG. 3, the time periods at high voltage are shown to have about the same duration as the time periods at low or zero volts in the voltage wave form, it will be understood that this is not required and that wave forms with unequal time periods at the high and low voltages can be used as well and are within the scope of the invention. Since time is required for measurements to be taken, it is preferable that the frequency or duty cycle of the wave form does not exceed 10 Hz. Voltages and electrical fields of other waveforms may be used and are within the scope of the invention. For example, the voltage wave form may be a sine wave that is at low magnitudes for a time period long enough for detection to occur.

If a electrochemical parameter of the separated components of the sample can be detected quickly within a short time period, it may not be necessary to detect such parameter intermittently, as long as there is at least one adequate time period for measurement during which the electrical field at or near the electrode 24 is below a predetermined value or bears a certain low ratio to the electrical field applied during separation of the sample. The parameter is then measured during such at least one time period.

To determine a peak in an electropherogram, it is preferable for 10 or more data points to be taken. In capillary zone electrophoresis employing electroosmotic flow, a sampling rate of 1 to 10 Hz is usually adequate. Therefore, if the voltage applied to the tube oscillates at 10 Hz, and the sampling rate is at 10 Hz, that means one data point can be taken during the low voltage portion of each cycle of the voltage. It is of course possible to use a voltage with a wave form that is at low voltage(s) for 1 second in order for 10 data points to be taken at 10 Hz sampling rate. For improved efficiency, it may be preferably to employ a voltage that oscillates at 10 Hz instead.

In gel-filled columns, the analyte bands may be narrower than in capillary zone electrophoresis, and the sampling rate may be at about 50 Hz so that the applied voltage can be adjusted accordingly. Since no data is taken before the first sample component reaches the detector, it may be preferable to apply non-oscillating high voltage(s) for efficient separation of the sample until it is estimated that the first sample components may reach the detector soon, at which time a voltage such as that shown in FIG. 3 is applied instead.

In the embodiments above, the voltage source 22 or 104 applies voltages across the ends 12a, 12b of tube 12; it will be understood that such voltages may be applied across only a portion of the tube instead and the advantages of the invention described above will still apply. While the invention has been described above by reference to various embodiments, it will be understood that changes and modifications may be made without departing from the scope of the invention.

What is claimed is:

1. A method for electrokinetic separation and detection, comprising:

introducing a sample to be separated into a capillary tube;

applying an electrical potential across a portion of the capillary tube to cause electrokinetic separation of the sample into its components, said applying step being such that magnitude of the electrical field in a section of the tube is intermittently below a predetermined value for a plurality of time periods, and is above said predetermined value at other time periods; and intermittently measuring at least one electrochemical parameter of the separated components during said plurality of time periods.

2. The method of claim 1, wherein during the plurality of time periods, the electrical field has a magnitude that is less than about one-fifth of the magnitude of the electrical field at other time periods.

3. The method of claim 2, wherein said applying step is such that the electrical field in the section is in the shape of a square pulse between a high value above the predetermined value, and a low value at or below the predetermined value.

4. The method of claim 1, wherein said predetermined value is about 100 volts/cm.

5. The method of claim 1, wherein said tube has an outlet through which the separated components exit the tube, and wherein said measuring step includes detecting said parameter at or near the outlet of the tube.

6. The method of claim 1, said tube having an inlet and an outlet, wherein the applying step applies an electrical potential across the inlet and the outlet.

7. The method of claim 1, wherein said applying step applies a periodic electrical signal at a frequency less than about 10 Hz.

8. A method for electrokinetic separation and detection, comprising:

introducing a sample to be separated into a capillary tube;

applying an electrical field in a portion of the capillary tube to cause electrokinetic separation of the sample into its components such that during at least one time period when the electrical field is applied, the electrical field in a section of the tube has a magnitude that is less than about one-fifth of the magnitude of the electrical field at other times or time periods when the electrical field is applied; and measuring at least one electrochemical parameter of the separated components during said at least one time period.

9. The method of claim 8, wherein said applying step is such that the electrical field in the section is in the shape of a square pulse between a high value, and a low value less than about one-fifth of the magnitude of the high value.

10. The method of claim 8, wherein the electric field at other times or time periods is about 100 volts/cm.

11. The method of claim 8, wherein said tube has an outlet through which the separated components exit the tube, and wherein said measuring step includes detecting said parameter at or near the outlet of the tube.

12. The method of claim 8, said tube having an inlet and an outlet, wherein the applying step applies an electrical potential across the inlet and the outlet.

13. The method of claim 8, said applying step being such that the electrical field in the section is intermittently below a predetermined value for a plurality of time periods, and is above said predetermined value at other time periods; and wherein said measuring step includes intermittently measuring at least one electrochemical parameter of the separated components during said time periods.

14. The method of claim 13, wherein said applying step applies a periodic electrical signal at a frequency less than about 10 Hz.

15. An apparatus for electrokinetic separation and detection, comprising:

a capillary tube;

a first means for introducing a sample to be separated into the capillary tube;

a second means for applying an electrical field across a portion of the capillary tube to cause electrokinetic separation of the sample into its components, said second means being such that magnitude of the electrical field in a section of the tube is intermittently below a predetermined value for a plurality of time periods, and is above said predetermined value at other time periods; and a third means for intermittently measuring at least one electrochemical parameter of the separated components during said plurality of time periods.

16. The apparatus of claim 15, wherein said tube has an outlet through which the separated components exit the tube, and wherein said third means includes an electrode at or near the outlet of the tube.

17. The apparatus of claim 15, said tube having an inlet and an outlet, wherein said second means applies an electrical potential across the inlet and the outlet.

18. The apparatus of claim 15, wherein said second means applies a periodic electrical signal at a frequency less than about 10 Hz.

19. An apparatus for electrokinetic separation and detection, comprising:

a first means for introducing a sample to be separated into a capillary tube;

a second means for applying an electrical field in a portion of the capillary tube to cause electrokinetic separation of the sample into its components such that during at least one time period when the electrical field is applied, the electrical field in a section of the tube has a magnitude that is less than about one-fifth of the magnitude of the electrical field at other times or time periods when the electrical field is applied; and a third means for measuring at least one electrochemical parameter of the separated components during said at least one time period.

20. The apparatus of claim 19, wherein said tube has an outlet through which the separated components exit the tube, and wherein said third means includes an electrode at or near the outlet of the tube.

21. The apparatus of claim 19, said tube having an inlet and an outlet, wherein said second means applies an electrical potential across the inlet and the outlet.

22. The apparatus of claim 19, wherein said second means applies a periodic electrical signal at a frequency less than about 10 Hz.

* * * * *